United States Patent
Rheinberger et al.

(10) Patent No.: US 7,189,344 B2
(45) Date of Patent: Mar. 13, 2007

(54) METHOD FOR PRODUCING A SYNTHETIC MATERIAL PART

(75) Inventors: Volker Rheinberger, Vaduz (LI); Gerhard Zanghellini, Schaan (LI); Wolfgang Wachter, Eschen (LI); Peter Kunkel, Triesen (LI)

(73) Assignee: Ivoclar Vivadent AG, Schaan (LI)

( * ) Notice: Subject to any disclaimer, the term of this patent is extended or adjusted under 35 U.S.C. 154(b) by 615 days.

(21) Appl. No.: 10/071,143

(22) Filed: Feb. 7, 2002

(65) Prior Publication Data

US 2002/0127345 A1 Sep. 12, 2002

Related U.S. Application Data

(60) Provisional application No. 60/328,897, filed on Oct. 12, 2001, provisional application No. 60/287,775, filed on May 1, 2001.

(30) Foreign Application Priority Data

Mar. 12, 2004 (DE) ................. 101 11 704

(51) Int. Cl.
*A61C 13/00* (2006.01)

(52) U.S. Cl. .......................... 264/16; 264/19

(58) Field of Classification Search ................ 264/401, 264/303, 16, 17, 18, 20, 19; 700/120; 523/120, 523/115
See application file for complete search history.

(56) References Cited

U.S. PATENT DOCUMENTS

| | | | | |
|---|---|---|---|---|
| 3,570,725 A | * | 3/1971 | Baker et al. | ................. 222/504 |
| 4,295,573 A | * | 10/1981 | Terry et al. | ................. 215/348 |
| 4,904,348 A | * | 2/1990 | Domes et al. | ................. 205/67 |
| 5,059,266 A | * | 10/1991 | Yamane et al. | |
| 5,121,329 A | * | 6/1992 | Crump | ....................... 700/119 |
| 5,164,128 A | * | 11/1992 | Modrek et al. | |
| 5,204,124 A | | 4/1993 | Secretan et al. | |
| 5,238,614 A | * | 8/1993 | Uchinono et al. | |
| 5,849,459 A | * | 12/1998 | Hagiwara et al. | |
| 5,880,756 A | | 3/1999 | Ishii et al. | |
| 5,902,537 A | * | 5/1999 | Almquist et al. | |
| 6,106,747 A | * | 8/2000 | Wohlwend | ................... 264/16 |
| 6,193,923 B1 | | 2/2001 | Jocelyn | |
| 6,322,728 B1 | * | 11/2001 | Brodkin et al. | ................ 264/19 |
| 6,849,308 B1 | * | 2/2005 | Speakman et al. | .......... 427/595 |
| 2002/0093115 A1 | * | 7/2002 | Jang et al. | ................... 264/113 |

FOREIGN PATENT DOCUMENTS

| | | |
|---|---|---|
| DE | 196 42 247 C1 | 1/1998 |
| DE | 19938463 A1 | 2/2001 |
| EP | 0 661 156 A | 7/1995 |
| GB | 2233928 A | 1/1991 |
| GB | 2 350 321 | * 11/2000 |
| WO | WO 01/13814 A | 3/2001 |

* cited by examiner

*Primary Examiner*—Brenda A. Lamb
(74) *Attorney, Agent, or Firm*—John C. Thompson; Alan S. Korman

(57) ABSTRACT

A method for producing a synthetic material part such as, for example, a dental restorative part, is provided and includes spray applying with a spray device a material having at least a polymerizable synthetic material onto a base in succeeding layers. Each layer of the spray applied material is substantially continuously polymerized by the spray device and has a viscosity which permits working of the applied material in an unpolymerized condition thereof with the spray device. The method also includes hardening the one or more of the already applied layers prior to the application of subsequent layers.

4 Claims, 2 Drawing Sheets

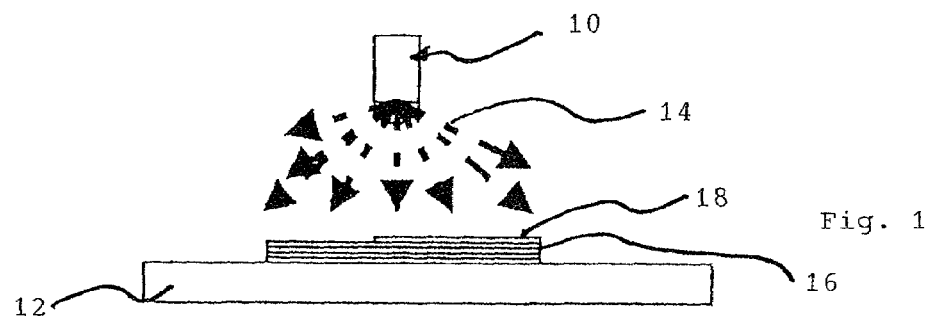
Fig. 1
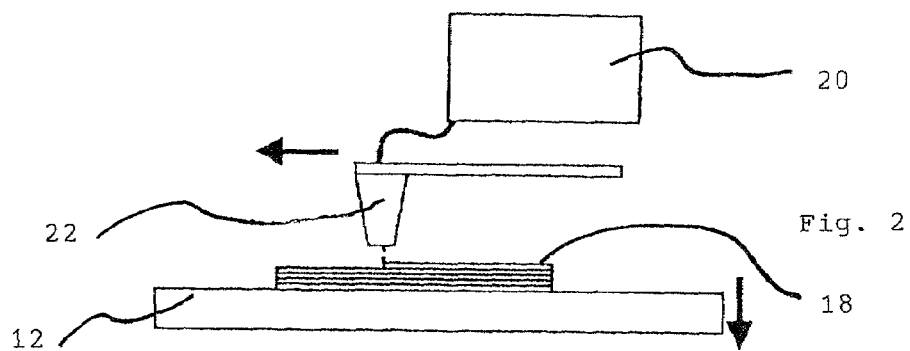
Fig. 2
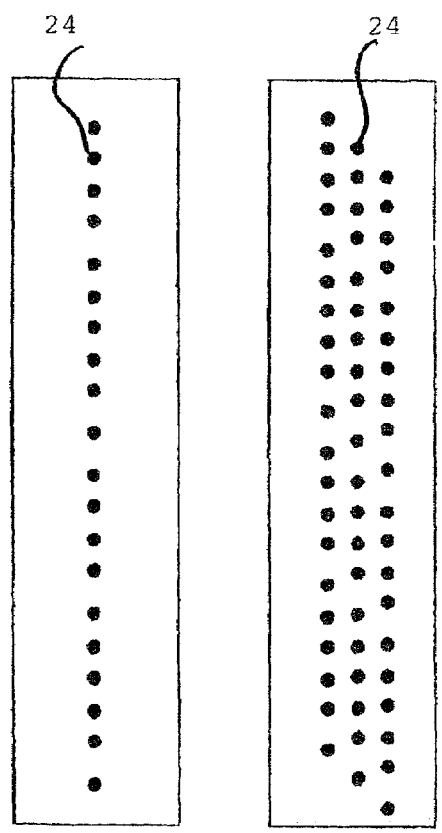
Fig. 3a
Fig. 3b

METHOD FOR PRODUCING A SYNTHETIC MATERIAL PART

CROSS-REFERENCE TO RELATED APPLICATIONS

This application claims foreign priority benefits under 35 U.S.C. §119(a)–(d) from German patent application ser. no. 101 11 704.3 filed Mar. 12, 2001. In addition, this application claims the benefit under 35 U.S.C. §119(e) of US provisional patent application Ser. No. 60/287,775 filed May 1, 2001, and U.S. provisional patent application Ser. No. 60/328,897 filed Oct. 12, 2001.

BACKGROUND OF THE INVENTION

The present invention relates to a method for producing a synthetic material part.

DE 196 42 247 discloses a method for producing a tooth replacement including an initial step of capturing three dimensional reproduction data and handling the data in preparation for the production of the tooth replacement. In this method, an electronically controlled machine tool is deployed to ensure the quick generation of a prototype. This method permits the precise production of a tooth replacement. However, the production method is decidedly expensive and requires an electronically controlled machine tool which performs the desired workpiece machining in a milling process.

The above-noted conventional method brings with it disadvantages due to the accompanying discarded material and unclean conditions, as these conditions cannot be tolerated in dental practice, even when dental labor is available for the task.

It is further conventionally known to use a three dimensional printing technology for the rapid production of prototypes. In this regard, two methods find usage: in a first method, which was developed by Massachusetts Institute Of Technology, a powder material, along with a binder medium, is applied by a spray device in layers built up to correspond to the object to be produced and the binder medium is hardened layer-by-layer and thereby binds to the powder material. In connection with the completion of the object by this first method, the excess, unbound powder material is removed. While the powder material enables this approach to offer flexibility in the configuration of the object to be produced, there typically remains a granular or gritty surface.

In another conventional method, the three dimensional printing technology is used in connection with the application of a material which is hardenable by contact with air and which is applied by electrostatic ink vapor spray jets. The spray device having the spray jets is similar to an ink vapor spray printing device and comprises comparatively more spray jets. In view of the fact that each applied material particle must be hardened completely, the production of an object by this method correspondingly requires a relatively long time.

Other conventional methods for the rapid production of objects have been elaborated and are commonly known as "Rapid Prototyping" methods. In this regard, such methods include the stereo lithography method, already developed during the 1980's by, in particular, 3D Systems Inc., by which a laser beam sculpts material in plate form based upon CAD data. Such devices require a considerable capital investment of, for example, a half million Deutschmarks or even a million Deutschmarks.

It has also been proposed to use laser sintering processes for the production of tooth replacement parts. These processes require in their own right the use of a high energy laser, which thus engenders various disadvantages.

SUMMARY OF THE INVENTION

The present invention provides a method for producing a synthetic material part including, in particular, a dental restorative part, which solves the challenge of reducing the capital investment cost while nonetheless providing a rapid production of the synthetic material part.

The method of the present invention, as compared to the conventional methods, permits the use of relatively larger spray drops for the reason that the complete hardening by means of light polymerization permits a rapid hardening of a just applied layer. This permits, as well, a cost favorable execution of the printing process so that the number of jets, which contribute substantially to the production cost burden, can be reduced. The relatively larger spray drops nonetheless permit a more rapid build up of the synthetic material part or object to be produced, whereby, in accordance with a particularly advantageous embodiment of the present invention, the hardening of the just applied layer is initially only partially completed and the further hardening of the layer to its complete hardened condition is only performed after the layer has been overlaid by the next layer. This provides, moreover, the particular advantage that there is a better interconnection or bonding of the layers to one another. In accordance with the present invention, it is particularly beneficial to prepare a dental restorative part comprised of an incomplete polymerizable monomer or oligomer. A dental restorative part of this type can be used in a particularly advantageous manner to produce a full prosthesis although it is also suitable for use in producing a partial prosthesis. Such prostheses exhibit considerable material strength which is provided by the uniform, complete hardening of the material.

In comparison to the conventional methods, the one requirement in performing the method of the present invention is to definitively optically shield the spray jet device during the light hardening step in order to prevent an obstruction of the spray jets due to intensive light radiation thereon.

Conventional light sources are suitable for use with the method of the present invention, whereby it is preferred to provide, in addition, ultraviolet components in the light hardening spectrum.

In accordance with a further, particularly advantageous aspect of the present invention, the method of the present invention can be directly employed in a dental practice. The method of the present invention does not produce any discard milling material or other debris; to this extent, the method is similar to those light hardening processes involving the disposition of a light hardening device in the mouth of a dental patient which dentists, in any event, frequently perform.

As regarded from a further, particularly advantageous viewpoint, the monomer used in the method of the present invention can comprise a wax like substance. This substance permits setting of the viscosity to a correct value at which a run off of the just applied spray drops used for the layer building is prevented while, on the other hand, the viscosity value is so small that it is possible to perform a penetration of the spray jet thereinto in a favorable manner. It is particularly advantageous if this wax-like substance comprises reactive groups which can be co-polymerized with the monomer. The spray applied material is a selected one of a material having a wax-like polymerizable substance having an ester of a carbon acid and a polymerizable alcohol and a material having an ester of an alcohol and a polymerizable carbon acid derivative of between about 20% to 99.99% by weight of the material.

The printing technology, which can be adaptively applied in the method of the present invention, principally corresponds to the proven ink spray printing method whereby it is to be understood that the spray devices can be adapted in a desired manner to the method of the present invention.

According to an advantageous embodiment of the present invention, it is provided thai the layer build up of the synthetic material part being produced is configured such that the color impression imparted by color imparting material built into the dental restorative part is accommodated to the natural color in the patient's mouth, and wherein the material which is spray applied is a polymerizable wax-like dental material having up to 70% by weight of at least one of a polymerizable monomer and oligomer, from 0.01 to 10% by weight of a polymerization initiator, and at least 20% by weight of a mixture having a selected one of wax-like and a flowable monomer and a color pigment, and the dental material has the property that one of its physical condition and its viscosity changes within a relatively small range of temperature. Note, the % by weight of a polymerization initiator in the polymerizable was-like material may also range form 0.5 to 5% or -0.5 to 2%.

In accordance with a further advantageous embodiment of the method of the present invention, the transparency of the respectively later applied layers is greater than that of the previously applied layers so that the dental restorative part has a color representatively corresponding to the natural colors in the patient's mouth. This embodiment of the method of the present invention is particularly advantageous for the production of tooth colored crowns, bridges, inlays, and onlays.

DETAILED DESCRIPTION OF THE PREFERRED EMBODIMENT

A commercially available printer operable for three dimensional printing processes can be used to produce a tooth replacement part in accordance with the method of the present invention, the printer being configured for performing the process developed by Massachusetts Institute of Technology involving the spray application and hardening of a powder material having a binder added thereto, with the method including the steps of applying layers of a polymerization initiator and a wax-like polymerizable substance to a polymerizable dental material comprising a polymerizable monomer or oligomer. The wax-like substance is an ester of an alcohol with a polymerization capable carbon acid derivative.

After the application of each layer, or after the application of several layers, the printing head having the spray device is blocked off by a black light protection cover which is moved via a linkage on the printing head and is operable to optically separate the printing head from the synthetic material. As soon as the stop position of the printing head is reached, a significantly strong halogen lamp having a high ultraviolet component is actuated for several seconds to effect a light hardening of the applied materials. Thereafter, the lamp is turned off and the next layer is applied. This cycle is repeated until the tooth replacement part has been fully completed. A heat hardening is then performed to ensure that the polymerization has been completed.

In one modification of the method of the present invention, during the time that the printing head is applying the next layer, the light source is blocked off instead of being turned off, whereby the operating life of the light source is lengthened.

BRIEF DESCRIPTION OF THE DRAWINGS

FIG. 1 is a view of an appliance for the realization of the procedure according to the invention in schematic form.

FIG. 2 is another view of the appliance in accordance with FIG. 1, during another step in the procedure.

FIGS. 3a and b show two different possible layouts of the nozzles according to the invention.

Figure 4:
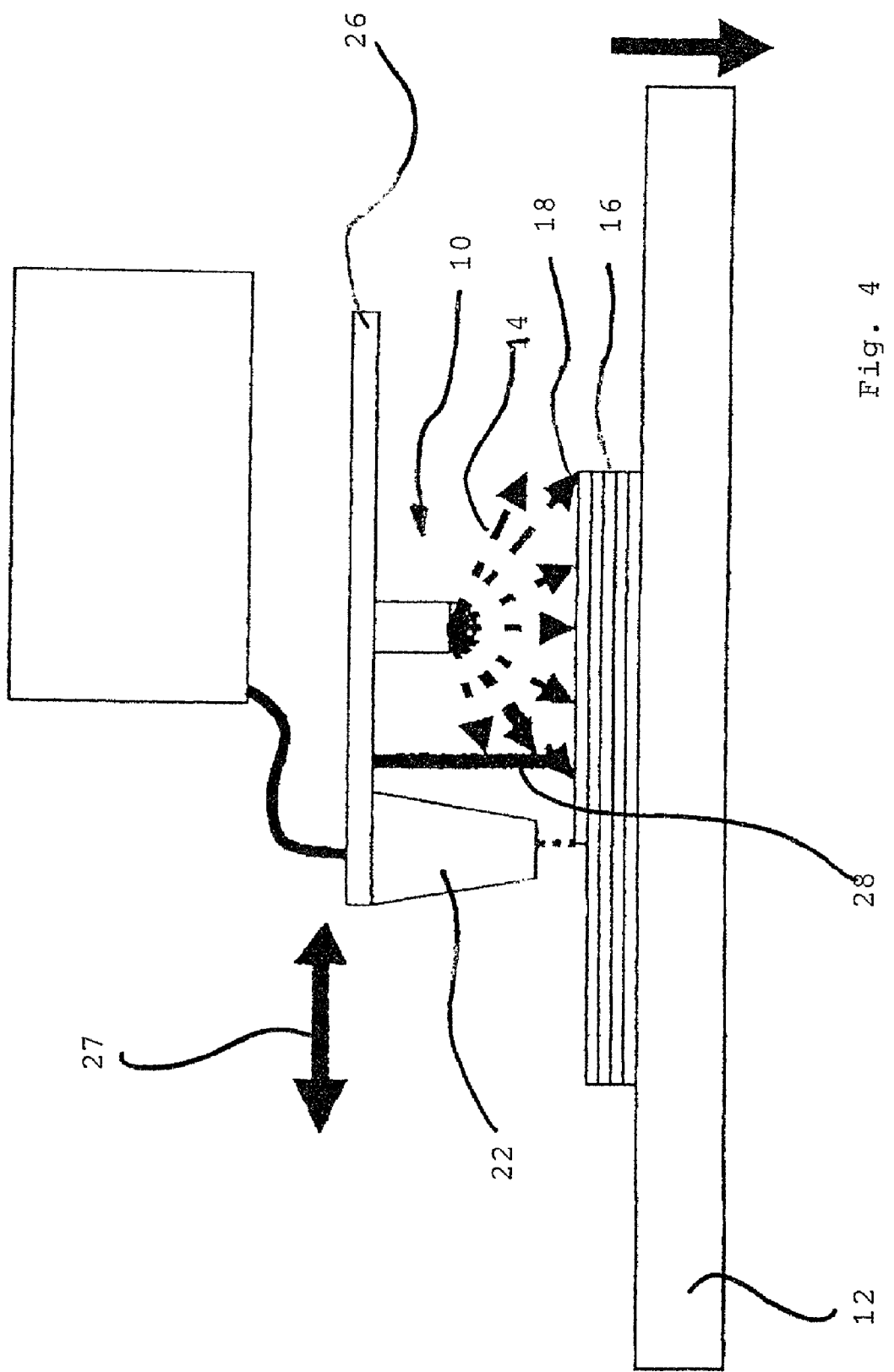
FIG. 4 is a modified design of an appliance for the realization of the procedure according to the invention.

From FIG. 1, an appliance for the realization of the procedure according to the invention is to be seen in schematic form. A nozzle layout 10 is provided, that is arranged with its nozzles on a base 12. The nozzle layout, which can for example be arranged in accordance with the two forms in FIG. 3, lets plastic material 14 emerge. The plastic material 14 is applied onto the base 12 in layers, where in the representation according to FIG. 1 four layers 16 are applied completely, while one layer 18 is only applied partially. For the application a relative motion takes place between the nozzle layout 10 and the base 12. For the manufacture of a dental restorative part, a stationarily installed nozzle layout 10 is preferred, while the base is movable horizontally.

The layers are applied preferentially in a low layer thickness that allows a precise formation of the restorative part, for example in a layer thickness of 100 microns. In accordance with a modified design, the layer thickness is even reduced to 20 microns.

The shaping of the restorative part can now take place so that material is applied in thicker layers at the positions at which raised forms should be realized, during which these surrounding areas are left free. For the realization of a complex three-dimensional restorative part, it is also possible to use the base 12 as a dividing-level and to form two separate part-restoration parts, which are secured together back to back. For precise fixing adjustment markings can be sprayed on, that can be removed after the parts have been secured together. The securing can for example be achieved through gluing, hot pressing or similar.

The applied restorative part is still soft at first and not capable of bearing a load. Through hardening by means of a polymerization device 20 in accordance with FIG. 2 the desired hardening can be achieved. In this regard a light source 22 is preferably provided, that like the nozzle layout 10 allows a relative movement against the base 12 as well. Spontaneous hardening takes precedence over light hardening every time if a layer 18 is applied.

It is understood that instead of pure light hardening, heat polymerization or a combination of these is also possible.

The base 12 is moreover vertically movable in order to account the layer construction of the layers 16 and 18 little by little.

From FIG. 3, two different possible nozzle layouts 24 are apparent. According to FIG. 3a, the nozzles are arranged in a row. By contrast, they are arranged in three rows according to FIG. 3b, where the rows are somewhat offset against each other. With the layout according to 3b, the resolution can still be somewhat improved.

A modified design is evident from FIG. 4. With this solution, the light source 22 and the nozzle layout 10 are secured to a common support 26. This solution allows the application of the plastic material 14 and hardening of the material in one step. In this regard a relative movement 12 takes place between the base 26 and the support 26 in accordance with the example of an implementation in accordance with FIGS. 1 and 2. For example the base 12 is moved from the right to the left in accordance with the arrow 27. By this means it is guaranteed that an observed area of the layer 16 is at first beneath the nozzle layout 10 and then below the light source 22.

In order to securely prevent premature hardening and also blockage of the nozzles of the nozzle layout 10, a shield 28 is provided between the nozzle layout 10 and the light source that extends to the layer 18. The shield 28 is preferably soft at least in its lower area so that it doesn't impair the layer construction of the uppermost layer 18. For example, a thin curtain of black plastic foil can also be inserted.

The present invention is, of course, no way restricted to the specific disclosure of the specification and drawings, but also encompasses any modifications within the scope of the appended claims.

What is claimed is:

1. A method for producing a synthetic dental restorative part such as a full or partial dental prosthesis, comprising:
   providing a base;
   spray applying with a spray device a material having at least a polymerizable synthetic material onto the base in succeeding layers such that each layer of the spray applied material is polymerized by a light source, the material includes a wax like substance having a viscosity such that a run off of the just applied spray drops used for the layer building is prevented while, on the other hand, the viscosity value is so small that it is possible to perform a penetration of the spray jet thereinto in a favorable manner; and
   hardening at least one already applied layer prior to the application of subsequent layers to form the dental restorative part; and wherein the material which is spray applied is a polymerizable wax-like dental material having up to 70% by weight of at least one of a polymerizable monomer and oligomer, from 0.01 to 10% by weight of a polymerization initiator, and at least 20% by weight of a mixture having a selected one of wax-like and a flowable monomer and a color pigment, and the dental material has the property that one of its physical condition and its viscosity changes within a relatively small range of temperature flux.

2. A method for producing a synthetic dental restorative part such as a full or partial dental prosthesis, comprising:
   providing a base;
   spray applying with a spray device a material having at least a polymerizable synthetic material onto the base in succeeding layers such that each layer of the spray applied material is polymerized by a light source, the material includes a wax like substance having a viscosity such that a run off of the just applied spray drops used for the layer building is prevented while, on the other hand, the viscosity value is so small that it is possible to perform a penetration of the spray jet thereinto in a favorable manner, wherein the spray applied material is a selected one of a material having a wax-like polymerizable substance having an ester of a carbon acid and a polymerizable alcohol and a material having an ester of an alcohol and a polymerizable carbon acid derivative of between about 20% to 99.99% by weigh; of the material; and
   hardening at least one already applied layer prior to the application of subsequent layers to form the dental restorative part wherein each layer is polymerized prior to the application thereonto of the next layer to a polymerized condition which is less than complete polymerization yet is such that the layer supports the retention of the next layer applied thereon.

3. A method for producing a synthetic dental restorative part such as a full or partial dental prosthesis, comprising:
   providing a base;
   spray applying with a spray device a material having at least a polymerizable synthetic material onto the base in succeeding layers such that each layer of the spray applied material is polymerized by a light source, the material includes a wax like substance having a viscosity such that a run off of the just applied spray drops used for the layer building is prevented while, on the other hand, the viscosity value is so small that it is possible to perform a penetration of the spray jet thereinto in a favorable manner; and
   hardening at least one already applied layer prior to the application of subsequent layers to form the dental restorative part; and wherein the material which is spray applied is a polymerizable wax-like dental material having up to 70% by weight of at least one of a polymerizable monomer and oligomer, from 0.01 to 10% by weight of a polymerization initiator, and at least 20% by weight of a mixture having a selected one of wax-like and a flowable monomer and a color pigment, and the dental material has the property that one of its physical condition and its viscosity changes within a relatively small range of temperature flux, wherein the polymerization initiator is between 0.5 to 5% by weight of the wax-like dental material.

4. A method for producing a synthetic dental restorative part according to claim 3, wherein the polymerization initiator is between 0.5 to 2% by weight of the wax-like dental material.

* * * * *